United States Patent [19]
Bigand et al.

[11] Patent Number: 6,112,623
[45] Date of Patent: Sep. 5, 2000

[54] TOOL FOR SCREWING A SCREW HAVING TWO THREADED PORTIONS SEPARATED BY AN INTERMEDIATE SCREWING PORTION

[75] Inventors: Dominique Bigand, La Morlaye; Jacques Clauze, Baigts de Bearn; Jose Gournay, Dammartin-En-Goele; Jean-Charles Moreau, Gouvieux; Jean Saurat, Avrille, all of France

[73] Assignee: Sofamor S.N.C., Cedex, France

[21] Appl. No.: 09/086,081

[22] Filed: May 28, 1998

[30] Foreign Application Priority Data

May 30, 1997 [FR] France ................... 97 06696

[51] Int. Cl.⁷ .................................................. B25B 13/00
[52] U.S. Cl. ............................................. 81/59.1; 81/451
[58] Field of Search ............... 81/59.1, 439, 451–453, 81/455, 456, 457; 606/104

[56] References Cited

U.S. PATENT DOCUMENTS

| | | | |
|---|---|---|---|
| 4,140,161 | 2/1979 | Russo et al. | 145/52 |
| 4,275,893 | 6/1981 | Bilanceri | 279/64 |
| 4,581,962 | 4/1986 | Marbourg | 81/451 |
| 5,352,231 | 10/1994 | Brumfield et al. | 606/99 |
| 5,484,440 | 1/1996 | Allard | 606/73 |
| 5,490,683 | 2/1996 | Mickel et al. | 279/75 |
| 5,498,265 | 3/1996 | Asnis et al. | 606/73 |
| 5,509,332 | 4/1996 | Donaldson, Jr. | 81/59.1 |
| 5,649,931 | 7/1997 | Bryant et al. | 606/104 |
| 5,651,294 | 7/1997 | Shiao | 81/59.1 |

FOREIGN PATENT DOCUMENTS 0 387 392 A2  9/1990  European Pat. Off. ........ A61B 17/16

*Primary Examiner*—James G. Smith
*Assistant Examiner*—David B. Thomas
*Attorney, Agent, or Firm*—Woodard, Emhardt, Naughton, Moriarty & McNett

[57] ABSTRACT

A tool for driving a screw having two threaded shanks separated by an intermediate portion. The tool includes a rod having a tapped end portion adapted to engage one of the threaded shanks. The tool also includes a cage adapted to receive the intermediate portion of the screw therein. The cage is provided with at least one opening containing a rolling member configured to be applied against a surface of the intermediate portion of the screw. The tool additionally includes a tube surrounding the rod and the cage. The tube includes an inner wall having a profile configured such that as the tube is rotated about the longitudinal axis, the inner surface applies a radial force to the rolling member, causing the rolling member to be radially displaced through the opening in the cage and placing it in abutment with the intermediate portion of the screw.

22 Claims, 4 Drawing Sheets

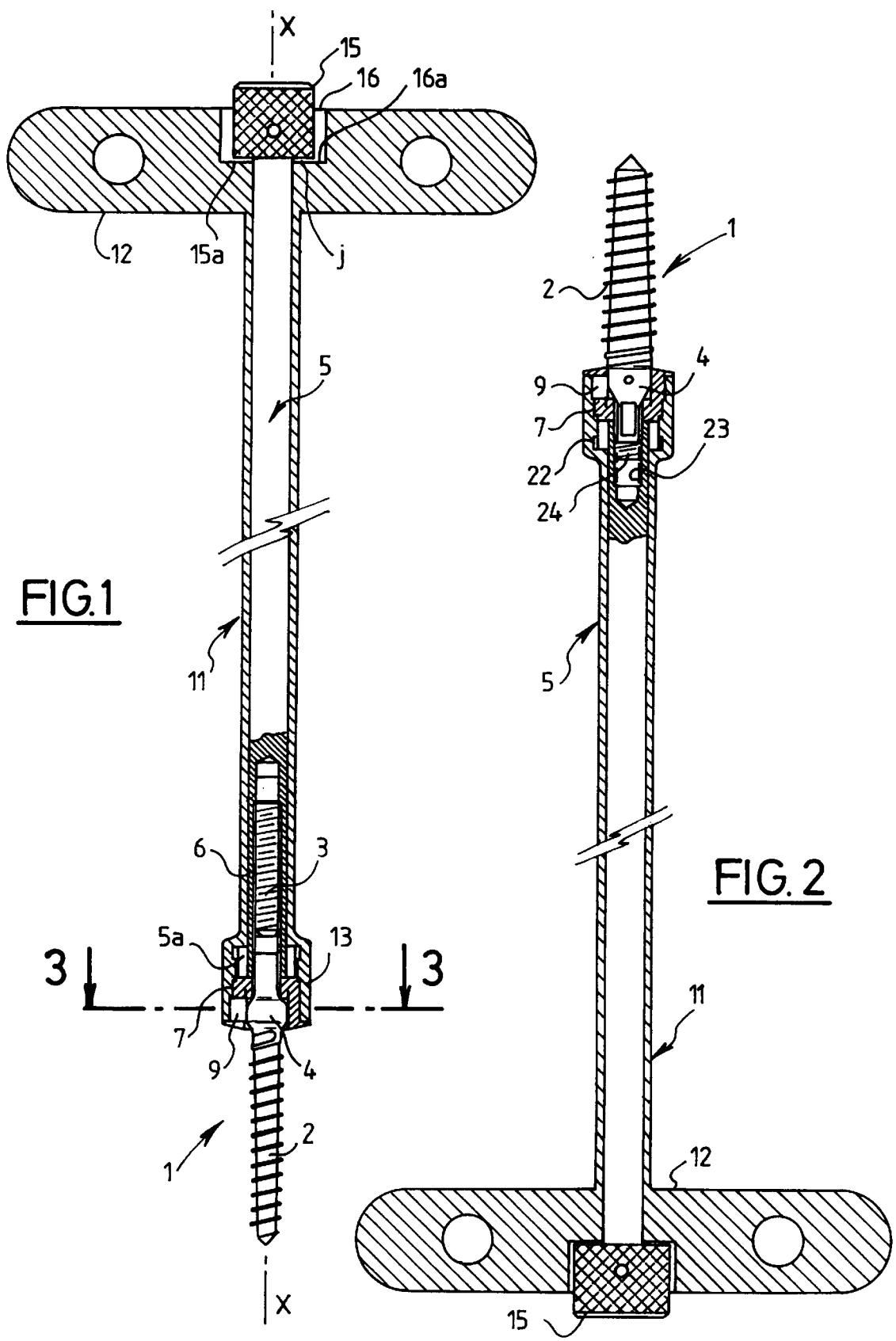

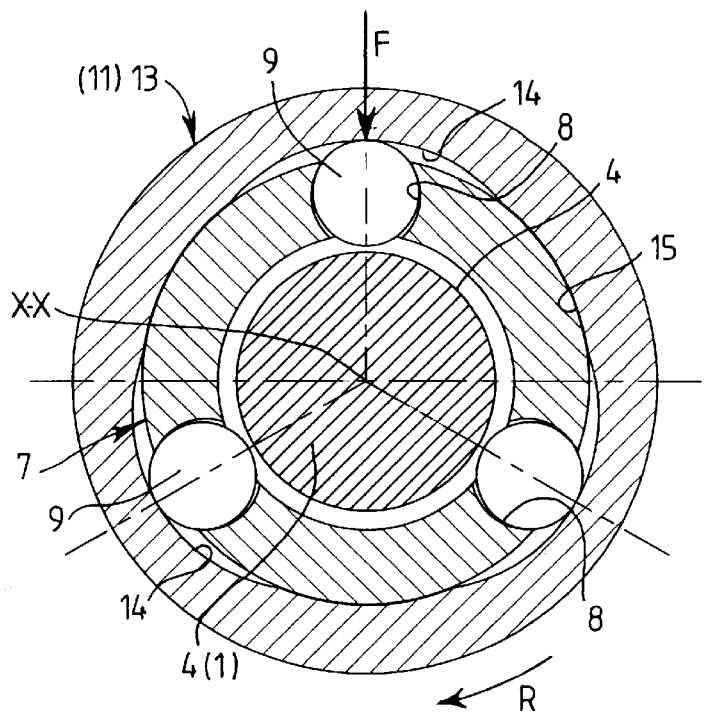
FIG. 3
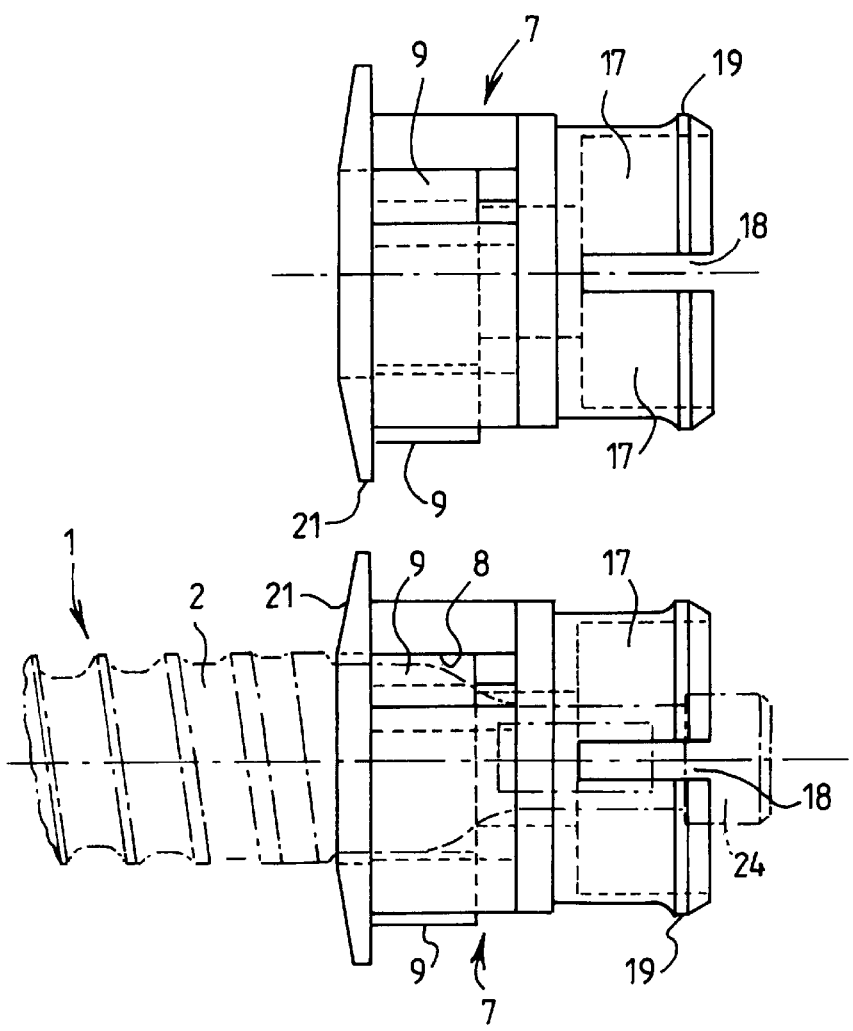
FIG. 4
FIG. 5

TOOL FOR SCREWING A SCREW HAVING TWO THREADED PORTIONS SEPARATED BY AN INTERMEDIATE SCREWING PORTION

BACKGROUND OF THE INVENTION

The present invention relates to a tool for screwing a screw having two threaded shanks separated by an intermediate portion provided for receiving screwing means.

Such a tool has many surgical applications, in particular in thoracoscopy and spinal osteosynthesis . . . , for placing screwed implants in position.

Screws are known which have two threaded shanks of different pitches in the extension of each other and separated by an intermediate engaging portion for screwing. Screws of this type are disclosed in particular in the document EP-A-0 612 507. The intermediate portion between the two threaded portions may be spherical, conical, or hexagonal, etc. In the case where this portion is spherical or conical, it has two lateral notches to allow the engagement of a screwing tool. These notches are difficult for the surgeon to find during the surgical intervention, constitute fracture initiators, and require a special machining station, which results in additional cost when manufacturing the screw.

Further, the engaging portion formed by a hexagonal screwing shape, considerably increases the overall size of the screw, which constitutes a further drawback.

An object of the invention is therefore to provide a screwing tool which is easily used by the surgeon in the course of the intervention and is of great strength.

SUMMARY OF THE INVENTION

According to the invention, the screwing tool comprises:

a rod having a tapped end portion adapted to be screwed on one of the two threaded portions, a tubular cage disposed in the extension of the end of the rod and in contact with the latter, said cage being adapted to cap said intermediate screwing portion and provided with at least one opening containing a rolling member applicable against the surface of said intermediate portion by an outer radial force, a tube surrounding the cage and the rod and provided with means for driving it in rotation about its longitudinal axis, the inner wall of which tube is in contact with said rolling member and has a profile which is such that a rotation of the tube radially displaces the rolling member through the cage and places it in a gripping position of abutment against said intermediate portion of the screw.

With such a structure, a small rotation of the outer tube about its axis places the rolling members on the spherical or cylindrical portion of the screw which can then be screwed or unscrewed by means of this gripping.

According to one embodiment of the invention, the tool comprises a plurality of rolling members constituted by rollers disposed with clearance in openings which are evenly angularly spaced apart in the cage.

These rollers may be for example cylindrical and exert a uniformly distributed pressure on the screwing portion of the implant.

According to another embodiment of the invention, the screwing tool comprises;

a rod having a tapped end portion adapted to be screwed on one of the two threaded portions, an outer tube containing the rod and in one end of which the screw can be partly inserted so that one of its threaded portions can be screwed in the rod, said tube being provided with means for driving it in rotation about its longitudinal axis, a transverse cam extending diametrally through said end portion of the tube, adapted to receive the screw and connected to rotate with the tube, a first element for gripping the screw, interposed in the tube with clearance between the cam and the adjacent end portion of the tube, and having a profile which is such that said first element is movable in axial translation and applicable on said intermediate portion of the screw by rotation of the tube and cam about the longitudinal axis of the tube.

Thus a rotation of the outer tube about its axis also turns the cam about the same axis, which causes said element to be firmly applied on the screwing portion of the screw. This element may be formed for example by a collar having an interior profile complementary to that of the screwing portion against which it bears.

Further features and advantages of the invention will be apparent from the following description with reference to the accompanying drawings which illustrate several embodiments of the invention by way non-limitative examples.

BRIEF DESCRIPTION OF THE DRAWINGS

FIG. 1 is a longitudinal sectional view of a first embodiment of the screwing tool according to the invention, and a longitudinal elevational view of a screw having two threaded portions engaged in one end of the tube.

FIG. 2 is a view similar to FIG. 1 of an alternative embodiment of the tube.

FIG. 3 is a cross-sectional view on line 3/3 of FIG. 1 to a larger scale.

FIG. 4 is a side elevational view to a larger scale of the cage of the screwing tool of FIGS. 1 and 2.

FIG. 5 is a view of the cage of FIG. 4 in which the screw having two threaded portions according to FIG. 2 is partly inserted.

DESCRIPTION OF THE PREFERRED EMBODIMENTS

Figure 6:
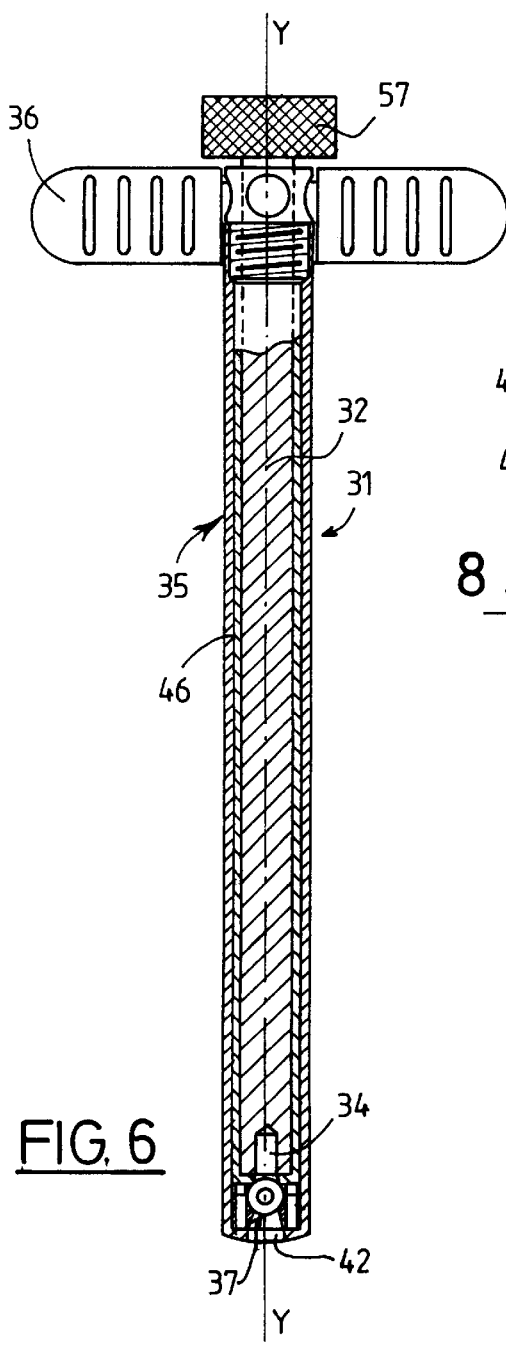
FIG. 6 is a longitudinal sectional view of a second embodiment of the screwing tool according to the invention.

The tool shown in FIGS. 1 to 5 is adapted to screw a screw 1 having two threaded shanks 2, 3 disposed in the extension of each other and separated by an intermediate portion 4 provided for receiving screwing means. The threaded shanks 2 and 3 have different pitches and the gripping portion 4 for screwing may be for example spherical, conical, cylindrical or have a hexagonal contour.

Screws of this type are used in particular in orthopedic surgery to constitute bone anchorage implants anchored by means of their threaded shank 2.

The tool comprises;

a rod 5 having an end portion 6 which is tapped and adapted to be screwed on the threaded portion of the shank 3, the threaded shank 2 being adapted to be screwed, for example, in the pedicle of a vertebra for a spinal osteosynthesis instrumentation;

a tubular cage 7 disposed in the extension of the end 6 of the rod 5 and in contact with the latter; the cage 7 is adapted to cap the intermediate screwing portion 4 of the screw 1, this portion 4 having a cylindrical surface in the illustrated embodiment. The tubular cage 7 is provided with a plurality of openings, namely three openings 8 in the presently-described embodiment, which are evenly angularly spaced apart around the screwing portion 4; these openings 8 each contain a rolling member 9 formed by a roller which is applicable against the surface of the intermediate portion 4 by an outer radial force F (FIG. 3).

The tool further comprises an outer tube 11 surrounding the cage 7 and the rod 5. This outer tube 11 is provided with means for driving it in rotation about its longitudinal axis XX, constituted in the illustrated embodiment by a transverse hand grip 12 formed at its end remote from that which receives the cage 7. The terminal portion 13 of the tube 11 remote from the grip 12 has a diameter substantially larger than the diameter of the rest of the tube 11 so as to surround without clearance the cylindrical cage 7. The inner wall of the terminal portion 13 has a suitable profile so that a rotation of the tube 11 about its axis XX exerts on the rollers 9 radial forces F which shift them against the screwing portion 4 of the screw 1.

In the embodiment illlustrated in FIG. 3, circular impressions 14 having a radius larger than the radius of the rest of the inner wall 15 of the portion 13 are formed in facing relation to each roller 9 symmetrically relative to the latter. It will therefore be understood that a rotation of the outer tube 11 in one direction or the other about its axis XX radially displaces the rollers 9, which are mounted with clearance in the openings 8 of the cage 7, until they are applied against the surface of the portion 4 with a force which depends on the torque exerted on the grip 12.

The rod 5 extends inside the outer tube 11, through the grip 12 and terminates in a rotatable manual control knob 15.

The knob 15 has a surface with asperities, for example is knurled, and is placed in a cavity 16 in the grip 12 with an operational clearance j defined between the bottom 16a of the cavity 16 and the transverse face 15a of the knob 15. Further, the rod 5 is axially freely movable inside the tube 11.

The tubular cage 7 is removably mounted in the end portion 13 of the tube 11, for example with the aid of clipping means which permit an easy extraction of the cage 7 from the end portion 13. In the described embodiment (FIGS. 4 and 5), these clipping means comprise a plurality of longitudinal flexible tongue portions 17, for example three tongue portions, which are separated by longitudinal slots 18 and each define an annular end boss 19. Remote from the tongue portions 17, the cage 7 is provided with a transverse flange 21 adapted to be applied against the end edge of the portion 13 of the tube 11 after the cage 7 has been inserted in this portion 13.

At the end of this axial insertion of the cage 7, the bosses 19 come to be resiliently engaged in a complementary groove 22 formed in the end of the inner wall of the end portion 13, which consequently maintains the cage 7 in position. To extract the latter when desired, it is sufficient to exert a pull on the flange 21 with a suitable tool.

Depending on the length of the threaded shank 3 of the screw 1, which varies in accordance with the type of screw, the tapped bore 6 may have a different corresponding length. Thus, in the embodiment of FIG. 2, the rod 5 comprises a bore 23 which is much shorter than the bore 6 for the purpose of receiving a corresponding threaded portion 24 which is shorter than the threaded portion 3, the rest of the tool being identical to the tool of FIG. 1.

More precisely, the bores 6, 23 constitute tapped holes capable of receiving threaded portions of the shanks 3, 24.

The use of the tool just described will be understood from the description.

A tool is chosen whose rod 5 has a bore 6 or 23 . . . of a length adapted to that of the screw 1 it is desired to use. The threaded rod 3 or 24 is inserted in the bore 6 or 23 and its end is screwed in the end tapped hole 6a or 23a. At the end of the screwing, the intermediate screwing portion 4 is located in the cage 7 radially in facing relation to the rollers 9, with the threaded shank 2 projecting out of the cage 7.

At the end of the screwing of the rod 5 on the threaded shank 3 or 23, the end of the rod abuts against the cage 7 and the aforementioned clearance j remains between the knob 15 and the bottom 16a of the cavity 16. Consequently, when the knob 12 is turned in one direction or the other to screw or unscrew the screw 1, the rollers 9 are applied against the surface of the portion 4 by the rotation of the impressions 14, and the screwing or the unscrewing is effected while maintaining the clearance j between the knob 15 and the bottom of the cavity 16. Owing to this clearance, the knob 15 cannot hinder the rotation of the grip 12 and consequently the screwing and unscrewing force exerted by the operator.

The operational clearance j is of importance for a satisfying use of the tool. Indeed, in the absence of this clearance at the end of the screwing, the knob 15 of the rod 5 would become jammed in the grip 12 and it would be necessary to exert a considerable force to unjam the tool 11 after the screwing of the screw 1 or on the contrary to unjam it.

A very small rotation of the tube 11 is sufficient to firmly grip the portion 4 by means of the rollers 9, which is an important advantage of the tool according to the invention.

Another advantage of this tool results from the presence of the cage 7. Indeed, in the absence of the latter, the end of the outer tube 11 may encounter soft regions o, on the contrary, hard points, for example, in surgery, soft tissues and hard points of bone. The latter would then cause the tube to rise and consequently stop the screwing or unscrewing. The interposed tubular cage 7 prevents this rise and therefore permits maintaining the screwing force in the aforementioned cases. This is particularly important owing to the short length of the guiding contact between the rollers 9 and the bearing surface of the portion 4 which may indeed be spherical.

Consequently, the tubular cage 7 guarantees the continuity and the effectiveness of the screwing-unscrewing operation.

In addition, the fact that this cage 7 is removable affords another advantage for cleaning purposes since it permits an easy disassembly of the tool 11 after, for example, a surgical intervention.

Further, at the end of the screwing of the rod 5 on the threaded portion 3, 24, the end 5a of the rod 5 abuts against the cage 7 (FIGS. 1 and 2). This abutment drives the cage 7 in rotation and consequently causes the rollers 9 to be pressed against the outer tube 11, these rollers and the cage 7 having therefore been displaced in rotation in the clockwise direction R (FIG. 3). Consequently, the driving in rotation of the tube 11 by the grip 12 is then effected without the time required for a prior engagement of the rollers, which advantageously causes the immediate gripping of the screw 1 by the rollers.

Figure 7:
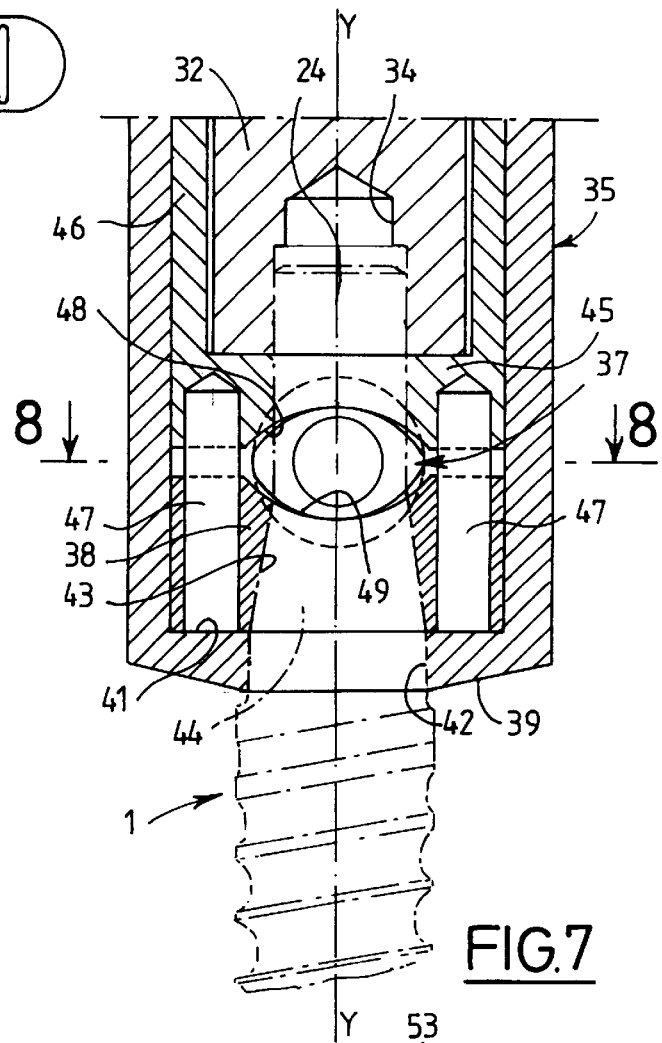
FIG. 7 is a partial longitudinal sectional view to a larger scale of the end portion of the tool of FIG. 6 in which the screw to be screwed or unscrewed is inserted.
Figure 8:
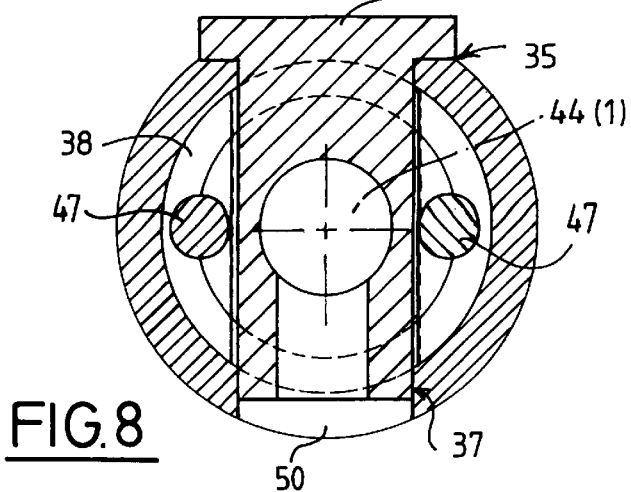
FIG. 8 is a cross-sectional view taken on line 8/8 of FIG. 7.
Figure 9:
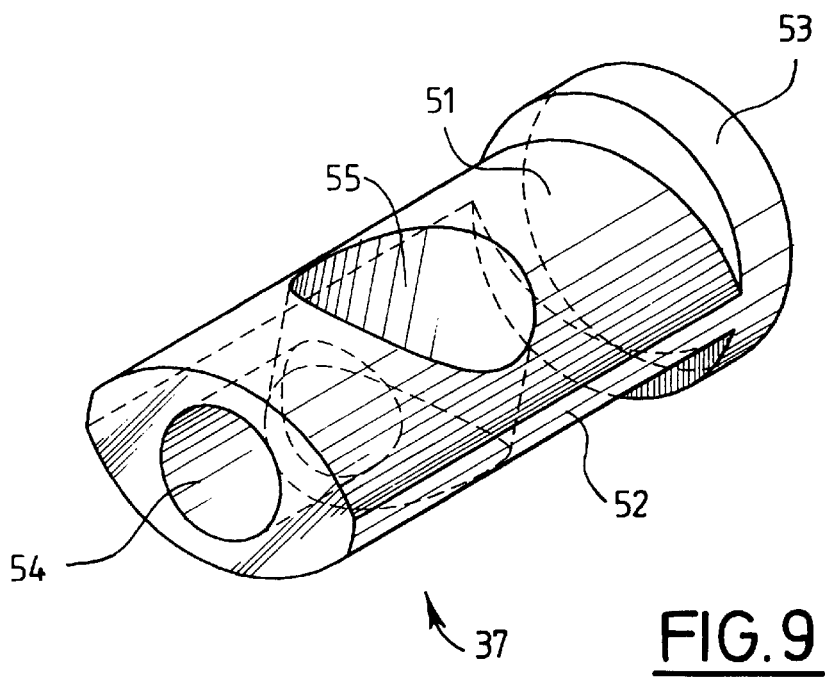
FIG. 9 is an elevational view to a larger scale of the cam of the tool of FIGS. 6 to 8.
Figure 10:
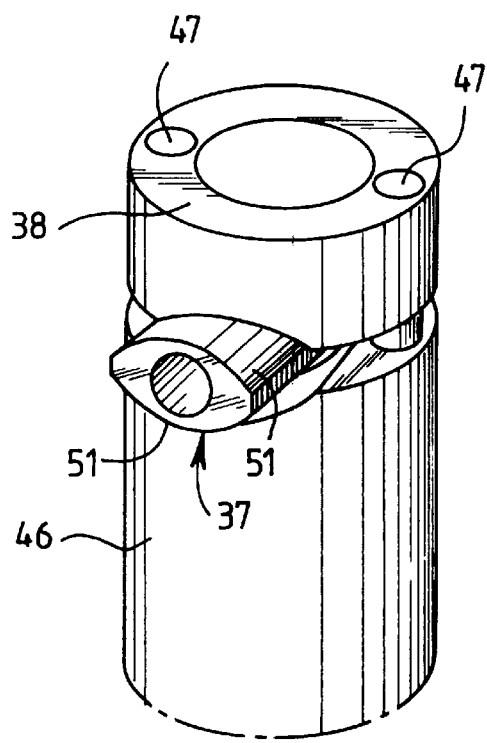
FIG. 10 is a partial perspective view to a larger scale of the tool of FIGS. 6 to 8 showing its transverse cam in the neutral position before gripping the screw.

A second embodiment of the screwing tool according to the invention will now be described with reference to FIGS. 6 to 10.

The tool comprises the following elements;

a rod 32 having a longitudinal axis YY and an end portion which includes an axial tapped hole 34 adapted to being screwed on one (24) of the two threaded portions 3, 24 of the screw;

an outer tube 35 having a longitudinal axis YY which contains the rod 32 and in one end of which the screw 1 can be partly inserted so that its threaded shank 24 (3a) can be screwed in the tapped hole 34; the tube 35 is provided with means for driving it in rotation along its longitudinal axis YY, namely an end grip 36 provided at the end remote from the tapped hole 34, a transverse cam 37 extending diametrally through the end portion of the tube 35 adapted to receive the screw 1 and connected to rotate with the tube 35, a first element 38 interposed in the tube 35 with clearance between the cam 37 and the adjacent end 39 of the tube 35 and more precisely the inner wall 41 of the end 39. The latter is provided with a central opening 42 for inserting a screw 1 in the annular element 38, formed for example by a collar having a conical inner surface 43 adapted to cap a complementary conical surface of the screwing portion 44 of the screw 1.

In the described embodiment, the tool 31 comprises a second element 45 interposed between the cam 37 and the rod 32. The second element 45 constitutes the end of a tube 46 inserted between the rod 32 and the outer tube 35. The end portion 45 of the tube 46 is connected to the collar 38 by means which allow the collar 38 a certain amount of freedom in axial translation in the tube 35. In the embodiment illustrated in FIG. 7, these means comprise two longitudinal connecting pins 47 inserted in corresponding bores in the end 45 of the tube 46 and in the collar 43. The confronting faces 48, 49 of the elements 45 and 38 located on each side of the cam 37 have such profiles as to constitute surfaces which are complementary to the surface of the cam 37.

As the latter is, in the described embodiment, in the form of a bar which has an oval or substantially elliptic section or is an ellipsoid 51 (FIGS. 9 and 10) the surfaces 48, 49 situated between the pins 47 have a profile matching the two sides of the cam 37.

Longitudinal flat faces 52 are provided between the two ellipsoid faces 51. At one of its ends, the cam 37 is extended by a disc 53 while its other end is provided with a central opening 54 adapted to receive a stud (not shown) whereby it is possible to retain the cam 37 in the outer tube 35. The opposite ends of the cam 37 are engaged in the diametrally opposed openings 50 in the tube 35.

The cam 37 is provided in its central part with a through opening 55 for the passage of the screw 1 and more precisely its threaded portion 24. The end disc 53 forms an axial stop for a good positioning of cam 37 in regard to external tube 35. Indeed, the opening 55 for passage of the threaded portion 24 of screw 1 must be centered within the screwing tool 31. The disc 53 may be replaced by any equivalent means.

The rod 32 is provided with a manual shifting knob 57 which extends out of the grip 36 of the tube 35.

The tool just described is used in the following manner.

The screw 1 is inserted in the opening 42 of the tube 35, in the collar 38 and in the opening 55 of the cam 57. Then its threaded end portion 24 is screwed in the tapped bore 34 of the rod 32. The tool 31 and the screw 1 are then in the situation illustrated in FIG. 7.

The tube 35 is turned about its axis YY by the grip 36 and this also turns the cam 37 about the axis YY. This rotation exerts, by means of the opposite surfaces 51, opposing axial thrusts on the end 45 of the tube 46 and on the collar 38. As the tube 46 is locked against translation on the rod 32, only the collar 38 is displaced and applied against the portion 44 of the screw by sliding along the pins 47. As soon as the collar 38 firmly grips the portion 44, the screwing or the unscrewing of the screw 1 can be effected.

In an alternative embodiment, the inner rod 32 may include, as in the preceding embodiment, an inner tapped bore whose length is adapted to that of the threaded portion of the implant 1, for example a long tapped bore corresponding to the shank 3 of a screw 1.

It should be noted that each of the rods 5 and 32 may have its two opposite end portions provided with tapped holes 6, 23 of different lengths adapted to threaded shanks of corresponding lengths. Their actuating knobs 15, 57 are then fixed to the end which is unused for the chosen screw.

The two tubes just described may be used in any technical field requiring the screwing of a screw having two threaded shanks of different pitches interconnected by an intermediate screwing portion.

What is claimed is:

1. A surgical tool for driving a bone screw, the screw having a driving portion and a threaded shank extending therefrom, the surgical tool comprising:

a shaft defining a passage extending along a longitudinal axis of said shaft, said passage being bounded by an inner wall, said inner wall defining a bearing surface;

a cage disposed in said passage and being sized to receive the driving portion of the screw therein, said cage having a side wall defining at least one opening, said at least one opening receiving a radially displaceable member therein, said radially displaceable member being positioned between said bearing surface and the driving portion when the driving portion is received within said cage; and wherein said bearing surface exerts a radial force on said radially displaceable member in response to rotation of said shaft about the longitudinal axis, said radial force biasing said radially displaceable member toward the driving portion of the screw until said radially displaceable member engages the driving portion in a fixed bearing relationship when the driving portion is received within said cage, and wherein the screw rotates in response to further rotation of said shaft after establishment of said fixed bearing relationship.

2. The surgical tool of claim 1, wherein said displaceable member is configured to move in response to said radial force toward the driving portion until establishment of said fixed bearing relationship.

3. The surgical tool of claim 1, wherein said radially displaceable member is a roller, said roller turning in response to said rotation of said shaft and rolling along said bearing surface until establishment of said fixed bearing relationship.

4. The surgical tool of claim 3, wherein said roller is cylindrical-shaped and said bearing surface is arcuate.

5. The surgical tool of claim 1, wherein the driving portion of the screw has a generally circular outer cross section.

6. The surgical tool of claim 5, wherein the driving portion of the screw is at least partially spherically-shaped.

7. The surgical tool of claim 1, wherein said side wall defines a plurality of said openings uniformly spaced around the periphery of said cage, each of said openings receiving one of said radially displaceable members therein, said inner wall defining a plurality of said bearing surfaces uniformly spaced in correspondence with said openings.

8. The surgical tool of claim 1, further comprising means for removably securing said cage within said passage.

9. The surgical tool of claim 1, further comprising means for placing said radially displaceable member in an abutting relationship with the driving portion of the screw prior to said rotation of said shaft.

10. A surgical tool for driving a bone screw, the screw having opposing first and second threaded shanks extending from a driving portion, the surgical tool comprising:

a tube having a terminal portion, said tube defining a passage extending therethrough along a longitudinal axis of said tube, said passage being bounded by an inner wall, said inner wall defining a bearing surface adjacent said terminal portion;

a rod at least partially disposed in said passage and having a first end portion and an opposing second end portion, said first end portion defining a threaded passageway adapted to engage said second threaded shank;

a cage disposed in said passage adjacent said terminal portion and being sized to receive the driving portion of the screw therein, said cage having a side wall defining at least one opening, said at least one opening receiving a radially displaceable member therein, said radially displaceable member being positioned between said bearing surface and the driving portion when the driving portion is received within said cage; and wherein said bearing surface exerts a radial force on said radially displaceable member in response to rotation of said tube about the longitudinal axis, said radial force biasing said radially displaceable member toward the driving portion of the screw until said radially displaceable member engages the driving portion in a fixed bearing relationship when the driving portion is received within said cage.

11. The surgical tool of claim 10, wherein said radially displaceable member is configured to move in response to said radial force toward the driving portion until establishment of said fixed bearing relationship.

12. The surgical tool of claim 10, wherein said first end portion of said rod is adapted to engage said cage, said cage rotating in response to rotation of said rod to cause said bearing surface to bear against said radially displaceable member and radially move said radially displaceable member toward the driving portion of the screw until said radially displaceable member engages the driving portion in an initial abutting relationship when the driving portion is received within said cage.

13. The surgical tool of claim 10, wherein said side wall of said cage defines an outwardly extending lip, said inner wall of said passage defining a groove adjacent said terminal portion, said lip co-acting with said groove to removably secure said cage within said passage.

14. The surgical tool of claim 10, further comprising a handle operatively attached to said tube opposite said terminal portion to rotate said tube about the longitudinal axis, said rod having a knob operatively attached to said second end portion, said rod having a length such that when said first end portion engages said cage, said knob will be spaced apart from said handle.

15. A surgical tool for driving a bone screw, the screw having a driving portion and a threaded shank extending therefrom, the surgical tool comprising:

a shaft having a first end and an opposing second end, said shaft defining a passage extending from said first end along a longitudinal axis of said shaft, said shaft defining a thru-hole transverse to the longitudinal axis and intersecting said passage;

a cam member disposed in said thru-hole, said cam member defining a first bearing surface;

a collar member disposed in said passage between said cam member and said first end of said shaft, said collar member defining a second bearing surface facing said first bearing surface, said collar member defining an opening sized to receive the driving portion of the screw therein, said opening being bounded by a gripping surface; and wherein said cam member rotates in response to rotation of said shaft about the longitudinal axis to cause said first bearing surface to bear against said second bearing surface and move said collar member along the longitudinal axis to cause said clamping surface to fixedly bear against the driving portion of the screw when the driving portion is received within said opening.

16. The surgical tool of claim 15, wherein said first bearing surface is elliptical, and said second bearing surface is substantially complementary to said first bearing surface.

17. The surgical tool of claim 15, wherein the driving portion of the screw is conically-shaped, and said gripping surface has a conical-shape substantially complementary to the driving portion.

18. A surgical tool for driving a bone screw, the screw having opposing first and second threaded shanks extending from a driving portion, the surgical tool comprising:

a tube having a first end and an opposing second end, said tube defining a passage extending therethrough along a longitudinal axis of said tube, said tube defining a thru-hole transverse to the longitudinal axis and intersecting said passage;

a rod having a first end portion and an opposing second end portion, said first end portion disposed in said passage and defining a threaded passageway adapted to engage said second threaded shank;

a cam member disposed in said thru-hole, said cam member defining a first bearing surface;

a collar member disposed in said passage between said cam member and said first end of said tube, said collar member defining a second bearing surface facing said first bearing surface, said collar member defining an opening sized to receive the driving portion of the screw therein, said opening being bounded by a gripping surface; and wherein said cam member rotates in response to rotation of said shaft about the longitudinal axis to cause said first bearing surface to bear against said second bearing surface and move said collar member along the longitudinal axis to cause said clamping surface to fixedly bear against the driving portion of the screw when the driving portion is received within said opening.

19. The surgical tool of claim 18, further comprising an intermediate member disposed in said passage between said cam member and said first end portion of said rod, said collar member being operatively connected to said intermediate member so that said collar member may translate relative to said intermediate member along the longitudinal axis of said tube.

20. The surgical tool of claim 19, wherein said collar member defines a first set of apertures, said intermediate member defines a second set of apertures aligned with corresponding ones of said first set of apertures, and each aligned pair of said first and second apertures is adapted to slidably receive a pin therein.

21. The surgical tool of claim 19, wherein said first end portion of said rod is operable to engage said intermediate member and clamp said intermediate member tightly against said cam member.

22. The surgical tool of claim 19, wherein said opening extends through said collar member and is sized to receive said second threaded shank, said cam member defining a first thru-opening generally aligned with said opening in said collar and sized to receive said second threaded shank, said intermediate member defining a second thru-opening generally aligned with said first thru-opening and sized to receive said second threaded shank, said threaded passageway of said rod engaging said second threaded shank.

* * * * *